(12) United States Patent
Qin et al.

(10) Patent No.: US 10,526,634 B2
(45) Date of Patent: Jan. 7, 2020

(54) CELL LINE FOR SCREENING INFLUENZA VIRUS POLYMERASE ASSEMBLY INHIBITOR AND CONSTRUCTION METHOD THEREOF

(71) Applicant: Suzhou Institute of Systems Medicine, Suzhou (CN)

(72) Inventors: XiaoFeng Qin, Jiangsu (CN); Chunfeng Li, Jiangsu (CN); Zining Wang, Guangdong (CN); Taijiao Jiang, Jiangsu (CN)

(73) Assignee: Suzhou Institute of Systems Medicine, Suzhou (CN)

( * ) Notice: Subject to any disclaimer, the term of this patent is extended or adjusted under 35 U.S.C. 154(b) by 0 days.

(21) Appl. No.: 15/737,826

(22) PCT Filed: Dec. 28, 2016

(86) PCT No.: PCT/CN2016/112724
§ 371 (c)(1),
(2) Date: Dec. 19, 2017

(87) PCT Pub. No.: WO2017/114430
PCT Pub. Date: Jul. 6, 2017

(65) Prior Publication Data
US 2019/0203251 A1 Jul. 4, 2019

(30) Foreign Application Priority Data

Dec. 29, 2015 (CN) .......................... 2015 1 1008822

(51) Int. Cl.
| | | |
|---|---|---|
| A61K 39/00 | (2006.01) |
| A61K 39/145 | (2006.01) |
| A61K 39/395 | (2006.01) |
| C12N 15/11 | (2006.01) |
| C12N 15/90 | (2006.01) |
| C12Q 1/02 | (2006.01) |
| C12N 15/86 | (2006.01) |
| C12Q 1/6806 | (2018.01) |
| C12Q 1/6853 | (2018.01) |
| C12Q 1/686 | (2018.01) |
| C12Q 1/6897 | (2018.01) |

(52) U.S. Cl.
CPC ............ *C12Q 1/025* (2013.01); *C12N 15/86* (2013.01); *C12Q 1/6806* (2013.01); *C12Q 1/686* (2013.01); *C12Q 1/6853* (2013.01); *C12Q 1/6897* (2013.01)

(58) Field of Classification Search
CPC ............ C07K 2317/76; C07K 16/1018; A61K 2039/505; A61K 2039/545; A61K 39/12
See application file for complete search history.

(56) References Cited

FOREIGN PATENT DOCUMENTS

| | | | |
|---|---|---|---|
| CN | 101875946 A | | 11/2010 |
| CN | 102051345 A | | 11/2011 |
| CN | 104560879 A | | 4/2015 |
| CN | 105505880 | * | 4/2016 |
| CN | 105505880 A | | 4/2016 |

OTHER PUBLICATIONS

International Search Report which issued in corresponding PCT application No. PCT/CN2016/112724.
Fang, Shisong et al., "Construction of Anti-influenza Virus Drug Selection Based on Protein-protein Interaction among Polymerase Subunits", China Tropical Medicine, vol. 11, No. 2, Feb. 28, 2011.
Li, Juan et al., "Identification of Anti-influenza Virus Drug Selection System Based on the New Target RNA Polymerase", China Tropical Medicine, vol. 13, No. 5, May 31, 2015.

* cited by examiner

*Primary Examiner* — Barry A Chestnut
(74) *Attorney, Agent, or Firm* — Fish & Richardson P.C.

(57) ABSTRACT

Provided are a cell line PA/PB1 HEK293T (Teton) for screening an influenza virus polymerase assembly inhibitors and a construction method thereof. The PA/PB1 HEK293T (Teton) cell line is constructed by integrating a vector expressing PA-GlucC fusion protein and a vector expressing GlucN-PB1 fusion protein into a HEK293T (Teton) cell via a triple plasmid system of pMDLg/pRRE, pRSV-Rev and pMD2.G. The HEK293T (Teton) cell line is formed by transforming a TOP10 competent cell with a synthesized Teton-3G gene fragment ligated to a lentiviral vector FG.

4 Claims, 1 Drawing Sheet
Specification includes a Sequence Listing.

SEQUENCE LISTING

```
<160> NUMBER OF SEQ ID NOS: 5

<210> SEQ ID NO 1
<211> LENGTH: 32
<212> TYPE: DNA
<213> ORGANISM: Homo sapiens

<400> SEQUENCE: 1
atagcggccg caatggaaga ctttgtgcga ca                               32

<210> SEQ ID NO 2
<211> LENGTH: 34
<212> TYPE: DNA
<213> ORGANISM: Homo sapiens

<400> SEQUENCE: 2
ttggcgcgcc cttttagtgc atgtgtgagg aagg                             34

<210> SEQ ID NO 3
<211> LENGTH: 34
<212> TYPE: DNA
<213> ORGANISM: Homo sapiens

<400> SEQUENCE: 3
atagcggccg caatggatgt caatccgact ttac                             34

<210> SEQ ID NO 4
<211> LENGTH: 31
<212> TYPE: DNA
<213> ORGANISM: Homo sapiens

<400> SEQUENCE: 4
ttggcgcgcc ctttttgccg tctgagctct t                                31

<210> SEQ ID NO 5
<211> LENGTH: 747
<212> TYPE: DNA
<213> ORGANISM: Homo sapiens

<400> SEQUENCE: 5
atgtctagac tggacaagag caaagtcata aactctgctc tggaattact caatggagtc    60
ggtatcgaag gcctgacgac aaggaaactc gctcaaaagc tgggagttga gcagcctacc   120
ctgtactggc acgtgaagaa caagcgggcc ctgctcgatg ccctgccaat cgagatgctg   180
gacaggcatc atacccactc ctgccccctg gaaggcgagt catggcaaga ctttctgcgg   240
aacaacgcca agtcataccg ctgtgctctc ctctcacatc gcgacggggc taaagtgcat   300
ctcggcaccc gcccaacaga gaaacagtac gaaaccctgg aaaatcagct cgcgttcctg   360
tgtcagcaag gcttctccct ggagaacgca ctgtacgctc tgtccgccgt gggccacttt   420
acactgggct gcgtattgga ggaacaggag catcaagtag caaaagagga aagagagaca   480
cctaccaccg attctatgcc cccacttctg aaacaagcaa ttgagctgtt cgaccggcag   540
```

-continued

```
ggagccgaac ctgccttcct tttcggcctg gaactaatca tatgtggcct ggagaaacag    600
ctaaagtgcg aaagcggcgg gccgaccgac gcccttgacg attttgactt agacatgctc    660
ccagccgatg cccttgacga ctttgacctt gatatgctgc ctgctgacgc tcttgacgat    720
tttgaccttg acatgctccc cgggtaa                                        747
```

CELL LINE FOR SCREENING INFLUENZA VIRUS POLYMERASE ASSEMBLY INHIBITOR AND CONSTRUCTION METHOD THEREOF

TECHNICAL FIELD

The present disclosure relates to cell lines for screening influenza virus polymerase assembly inhibitors and a construction method thereof, which belong to the medical field.

RELATED ART

Influenza virus is a negative strand RNA virus, which may cause human acute upper respiratory tract infection and deaths. Seasonal influenza affects 5%-15% of the population worldwide, and leads to approximately 500 thousand deaths each year. According to different antigen types, influenza virus can be divided into three serologically distinct subtypes of A, B, and C, in which the most harmful subtype to humans is influenza A (subtype A) virus, including highly pathogenic avian influenza H5N1 and H7N9 virus, and H1N1 pandemic which occurred in 2009 and caused heavy loss of lives [1, 2].

Currently, major treatment methods for influenza are vaccines and small molecule drugs targeting membrane proteins HA, NA and M2. Since influenza virus mutates very fast, the virus that may become epidemic cannot be anticipated accurately, and vaccine mismatch will sometimes occur, which leads to reduced protective effect [3].

At present, drugs for influenza treatment are divided into two types according to the mechanisms of action: M2 ion channel protein inhibitors, such as amantadine; and NA inhibitors, such as oseltamivir, peramivir and zanamivir. M2 ion channel protein inhibitors have neurotoxicity, so that long-term administration may lead to defects such as drug resistant strains and ineffectiveness against influenza B; similarly, NA inhibitors also have drug resistant problems, thus, finding novel anti-influenza virus drugs and developing effective drug screening approaches is an on-going issue [4].

Influenza A virus genome consists of 8 strands of negative strand RNA, and each strand of virus RNA combines with nucleoproteins and RNA polymerase subunits (PB2, PB1, PA) to form a polymerase complex. The RNA polymerase subunits (PB2, PB1, PA) are crucial complexes responsible for the replication and transcription of influenza virus. The efficient assembly of this trimeric complex is the rate-limiting step of the RNA replication of the influenza virus, and is of major importance in influenza virus RNA synthesis and the production of viral progeny. In terms of evolution, the structure and function of different influenza virus polymerases are highly conserved, and drugs targeting influenza virus polymerase should have improved broad-spectrum property and less drug resistance compared to drugs targeting surface proteins [5, 6]. A plurality of polypeptides or small molecule inhibitors against influenza virus polymerase assembly have been reported, for example, $PB1_{1-25}$ and $PB1_{731-757}$ can disrupt PA-PB1 interaction and PB1-PB2 interaction respectively, and small molecule 361 can disrupt PA-PB1 interaction [7-9]. However, methods taken in those researches for screening such inhibitors are CoIP, BiFC or GST pull down, which are rather laborious, time consuming and difficult to perform.

In addition, the variety and number of naturally occurring small molecules are large; if inhibitors effective for inhibiting influenza virus polymerase assembly are to be screened from these small molecules, the use of a high efficient screening method is necessary. Current studies on influenza virus polymerase mainly utilize a micro replication system of the influenza virus polymerase, i.e., cells transient expressing PB2, PB1, PA, NP and RNA reporter gene. In order to detect influenza virus infection and screen inhibitors against influenza virus replication more efficiently, the RNA reporter gene needs to be transferred into cells to form a stably expressing cell line. However, currently, cell lines used for screening small molecule inhibitors against influenza virus polymerase assembly have not yet existed.

In view of the above, cell lines used for screening inhibitors against influenza virus polymerase assembly have a wide prospect of application.

References described in the related art above refer to the following respectively:

1. Stamboulian, D., Bonvehi, P. E., Nacinovich, F. M. & Cox, N. (2000) Influenza, *Infect Dis Clin North Am.* 14, 141-66.
2. Neumann, G., Chen, H., Gao, G F., Shu, Y. & Kawaoka, Y. (2010) H5N1 influenza viruses: outbreaks and biological properties, *Cell Res.* 20, 51-61.
3. de Jong, J. C., Beyer, W. E., Palache, A. M., Rimmelzwaan, G F. & Osterhaus, A. D. (2000) Mismatch between the 1997/1998 influenza vaccine and the major epidemic A(H3N2) virus strain as the cause of an inadequate vaccine-induced antibody response to this strain in the elderly, *J Med Virol.* 61, 94-9.
4. Boltz, D. A., Aldridge, J. R., Jr., Webster, R. G & Govorkova, E. A. (2010) Drugs in development for influenza, *Drugs.* 70, 1349-62.
5. Reuther, P., Manz, B., Brunotte, L., Schwemmle, M. & Wunderlich, K. (2011) Targeting of the influenza A virus polymerase PB1-PB2 interface indicates strain-specific assembly differences, *J Virol.* 85, 13298-309.
6. Resa-Infante, P., Jorba, N., Coloma, R. & Ortin, J. (2011) The influenza virus RNA synthesis machine: advances in its structure and function, *RNA Biol.* 8, 207-15.
7. Su, C. Y., Cheng, T. J., Lin, M. I., Wang, S. Y., Huang, W. I., Lin-Chu, S. Y., Chen, Y. H., Wu, C. Y., Lai, M. M., Cheng, W. C., Wu, Y. T., Tsai, M. D., Cheng, Y. S. & Wong, C. H. (2010) High-throughput identification of compounds targeting influenza RNA-dependent RNA polymerase activity, *Proc Nal Acad Sci USA.* 107, 19151-6.
8. Ghanem, A., Mayer, D., Chase, G., Tegge, W., Frank, R., Kochs, G, Garcia-Sastre, A. & Schwemmle, M. (2007) Peptide-mediated interference with influenza A virus polymerase, *J Virol.* 81, 7801-4.
9. Li, C., Ba, Q., Wu, A., Zhang, H., Deng, T. & Jiang, T. (2013) A peptide derived from the C-terminus of PB inhibits influenza virus replication by interfering with viral polymerase assembly, *FEBS J.* 280, 1139-49.
10. Morell, M., Czihal, P., Hoffmann, R., Otvos, L., Aviles, F. X. & Ventura, S. (2008) Monitoring the interference of protein-protein interactions in vivo by bimolecular fluorescence complementation: the DnaK case, *Proteomics.* 8, 3433-42.
11. Hu, C. D., Chinenov, Y. & Kerppola, T. K. (2002) Visualization of interactions among bZIP and Rel family proteins in living cells using bimolecular fluorescence complementation, *Mol Cell.* 9, 789-98.

SUMMARY

Problems to be Solved by the Disclosure

The purpose of the present disclosure is to provide a construction method of cell lines for screening inhibitors of an influenza virus polymerase assembly.

Means of Solving the Problems

The object of the present disclosure can be achieved by the following technical solutions:

A cell line for screening an influenza virus polymerase assembly inhibitor, the cell line is a PA/PB1 HEK293T (Teton) cell line with inducible PA/PB1 expression.

A construction method of the cell line for screening the influenza virus polymerase assembly inhibitor, the construction method comprises the following steps, S1. Plasmid construction: construct PA, PB1 plasmids; amplify influenza virus PA, PB1 genes by specific primers, and amplification products are subjected to dual enzyme digestion, followed by ligation to a vector, and PA, PB1 full length plasmids are extracted;

S2. Lentiviral expression vector construction: Gaussia Luciferase is cloned into a lentiviral vector as a reporter gene;

S2. Lentiviral vector construction: By clone techniques, the constructed PA, PB1 full length plasmids are integrated into the inducible lentiviral vector by homologous recombination to form pBiLC3-PA and pBiLC2-PB1;

S3. Construction of a 239T cell with stable Teton-3G protein expression: an inducible gene fragment, whose sequence is SEQ ID NO: 5, is ligated to the lentiviral vector FG by enzyme digestion, used for transformation of a TOP10 competent cell, and denoted as FG-Teton-3G, and FG-Teton-3G is stably expressed in the cell by a triple plasmid system of pMDLg/pRRE/, pRSV-Rev and pMD2.G.

S4. Construction of a cell line with inducible PA/PB1 expression: PA/PB1 is stably integrated into the HEK293T (Teton) cell by integrating the constructed pBiLC3-PA and pBiLC2-PB1 into the HEK293T (Teton) cell via the triple plasmid system, and finally, the PA/PB1 HEK293T (Teton) cell line with inducible PA/PB1 expression is formed.

Preferably, the amplification condition of the PA, PB1 genes in S1 is pre-denaturation at 95° C. for 5 min; followed by 30 cycles, each of which follows the condition below: denaturation at 95° C. for 30 s, annealing at 56° C. for 30 s, elongation at 72° C. for 2.5 min, and lastly, elongation at 72° C. for 10 min, The sequences of the specific primers used for amplifying influenza virus polymerase are SEQ ID NO: 1, SEQ ID NO:2, SEQ ID NO:3 and SEQ ID NO:4.

Preferably, the cell line is used for screening inhibitors against polymerase subunits PA-PB1 interaction of influenza virus.

Effect of the Disclosure

Inhibitors against influenza virus polymerase assembly can be screened efficiently, so that the desired inhibitors can be found more quickly, and efficiency is significantly improved.

DETAILED DESCRIPTION

The present disclosure specifically discloses a method for designing specific primers to amplify PA, PB1 genes of influenza virus from a WSN33 virus gene template, wherein the amplification condition is pre-denaturation at 95° C. for 5 min; followed by 30 cycles, each of which follows the condition below: denaturation at 95° C. for 30 s, annealing at 56° C. for 30 s, elongation at 72° C. for 2.5 min, and lastly, elongation at 72° C. for 10 min. Primer sequences described above are shown in Table 1.

TABLE 1

| Primer sequence list | | |
|---|---|---|
| SEQ ID NO: 1 | 2-PA-F | ATA GCGGCCGC A ATG GAAGACTTTGTGCGACA |
| SEQ ID NO: 2 | 2-PA-R | TT GGCGCGCC C TTTTAGTGCATGTGTGAGGAAGG |
| SEQ ID NO: 3 | 3-PB1-F | ATA GCGGCCGC A ATGGATGTCAATCCGACTTTAC |
| SEQ ID NO: 4 | 3-PB1-R | TT GGCGCGCC C TTTTTGCCGTCTGAGCTCTT |

Dual enzyme digestion was performed on PCR products and a pEntry vector (purchased from Invitrogen) using NotI and AscI (purchased from NEB), fragments were ligated to the pEntry vector using T4 ligase enzyme (purchased from NEB), and plasmids were extracted and preserved after verification by sequencing.

BiLC (Bimolecule Luminescence Complementation) Lentiviral Expression Vector Construction and Detection BiLC is short for Bimolecule Luminescence Complementation. Compared to BiFC (Bimolecule Fluorescence Complementation), BiLC uses Luciferase as a reporter gene, while BiFC uses fluorescent protein such as GFP or YFP as a reporter gene [10, 11]. Since the reaction of Luciferase is a chemiluminescent reaction catalyzed by enzymes, its sensitivity is much higher than simple light emission by GFP excitation, so that the sensitivity of BiLC method is much higher than that of BiFC method.

First, Gaussia luciferase was divided into N-terminus and C-terminus at amino acid residue 109, 16 amino acid residues at the N-terminus were deleted, the remaining N-terminus and the C-terminus were denoted as GlucN and GlucC, cloned into a lentiviral vector respectively, and denoted as pBiLC1-4, which could clone interested genes to N-terminus and C-terminus of GlucN and GlucC respectively.

Construction of BiLC Inducible Lentiviral Vector of PA and PB1

By the Gateway cloning technology, constructed PA and PB full length shuttle plasmids were integrated into the inducible (Teton) lentiviral BiLC expression vector by homologous recombination. pBiLC3-PA, expressing the fusion protein PA-GlucC, was formed by integrating PA into the pBiLC3 vector of lentiviral TRE; pBiLC2-PB1, expressing GlucN-PB1 fusion protein, was formed by integrating PB1 into the pBiLC2 vector of lentiviral TRE. Finally, verification was performed by sequencing.

Figure 1:
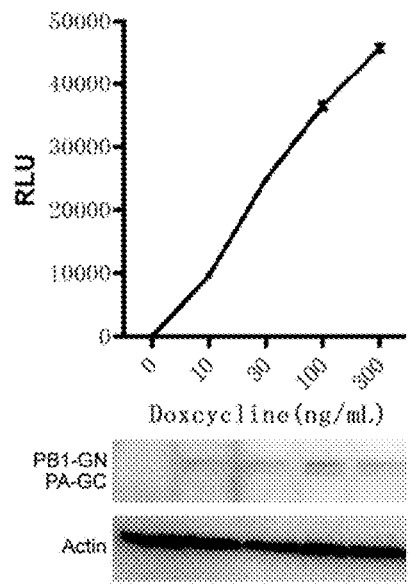
FIG. 1 is a schematic diagram of the influence of Doxycycline in a PA/PB1 HEK293T (Teton) cell line on PA/PB1 controlled inducible expression.
Figure 2:
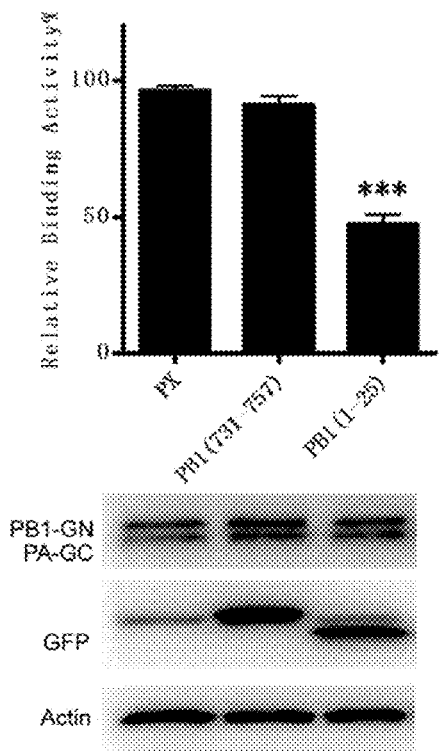
FIG. 2 is a schematic diagram of an inhibiting effect on PA-PB1 interaction detected by a cell line of the present disclosure.

Construction of a BiLC (Bimolecule Luminescence Complementation) HEK293T (Teton) Cell Line with Inducible PA/PB1 Expression (1) Construction of a HEK293T (Teton) Cell Line with Stable Teton-3G Expression A synthesized Teton-3G gene fragment (synthesized by Jierui Gene Corporation, the sequence is SEQ ID NO:5) was digested by enzymes, and ligated to the lentiviral vector FG by T4 enzyme (manufactured by NEB), used for transformation of TOP10 competent cells (purchased from Invitrogen), and was denoted as FG-Teton-3G herein. FG-Teton-3G was stably expressed in cells by a third generation lentiviral packaging system, i.e., a triple plasmid system of pMDLg/pRRE/, pRSV-Rev and pMD2., said cells was denoted as HEK293T (Teton). Specific operations can be divided into two steps, virus packaging and infection:

a. Lentiviral packaging: One day before transfection, HEK293T cells (ATCC: CRL-11268) and 500||L DMEM (purchased from Invitrogen) complete medium (10% FBS, purchased from Gibco) were plated in a 24 well plate (purchased from Thermo); transfection was performed when the cells reached a density of 50%-60%; 1 ug plasmid was used for transfection in each well, wherein the ratio of pMDLg/pRRE, pRSV-Rev, pMD2.G, and pFG-Teton-3G was 4:2:1:2. After 8 h of transfection, the culture medium was removed, and 1 mL fresh medium was supplemented. After 48 h, supernatant was collected into an EP tube, and centrifugation was performed at 2500 rpm for 4 min. Supernatant was transferred into a new EP tube for virus infection.

b. Virus infection: 18 h before virus collection, 10,000 HEK293T cells (ATCC: CRL-11268) were plated in a 96 well plate (purchased from Thermo) using 100 μL DMEM. Before infection, approximately 50 μL DMEM was removed. 6 ug/mL polybrene (purchased from Sigma) was added into the collected virus supernatant, mixed well, and about 100 μL virus supernatant was added into each well of the 96 well plates. After 6-8 h of infection, 50 μL culture medium in the 96 wells was removed, and 100 μL fresh medium was added. After 72 h, the cells could be transferred out of the 96 well plates for expansion culture, thus the HEK293T (Teton) cell line was obtained.

```
SEQ ID NO: 5:
ATGTCTAGACTGGACAAGAGCAAAGTCATAAACTCTGCTCTGGAATTAC

TCAATGGAGTCGGTATCGAAGGCCTGACGACAAGGAAACTCGCTCAAAA

GCTGGGAGTTGAGCAGCCTACCCTGTACTGGCACGTGAAGAACAAGCGG

GCCCTGCTCGATGCCCTGCCAATCGAGATGCTGGACAGGCATCATACCC

ACTCCTGCCCCCTGGAAGGCGAGTCATGGCAAGACTTTCTGCGGAACAA

CGCCAAGTCATACCGCTGTGCTCTCCTCTCACATCGCGACGGGGCTAAA

GTGCATCTCGGCACCCGCCCAACAGAGAAACAGTACGAAACCCTGGAAA

ATCAGCTCGCGTTCCTGTGTCAGCAAGGCTTCTCCCTGGAGAACGCACT

GTACGCTCTGTCCGCCGTGGGCCACTTTACACTGGGCTGCGTATTGGAG

GAACAGGAGCATCAAGTAGCAAAAGAGGAAAGAGAGACACCTACCACCG

ATTCTATGCCCCCACTTCTGAAACAAGCAATTGAGCTGTTCGACCGGCA

GGGAGCCGAACCTGCCTTCCTTTTCGGCCTGGAACTAATCATATGTGGC

CTGGAGAAACAGCTAAAGTGCGAAAGCGGCGGGCCGACCGACGCCCTTG

ACGATTTTGACTTAGACATGCTCCCAGCCGATGCCCTTGACGACTTTGA
```

-continued

```
CCTTGATATGCTGCCTGCTGACGCTCTTGACGATTTTGACCTTGACATG

CTCCCCGGGTAA
```

(2) Construction and Detection of a HEK293T (Teton) Cell Line with Inducible PA/PB1 Expression The constructed pBiLC3-PA and pBiLC2-PB1 were integrated into the HEK293T (Teton) cell by the third generation lentiviral packaging system, i.e., the triple plasmid system of pMDLg/pRRE/, pRSV-Rev and pMD2.G, so that PA/PB1 was stably integrated into the HEK293T (Teton) cell, and was denoted as PA/PB1 HEK293T (Teton) cell line. Virus packaging and infection steps were as described above.

To detect the influence of Doxycycline (Dox) (purchased from Sigma) on controlled inducible PA/PB1 expression, 100,000 PA/PB1 HEK293T (Teton) cells and 300 μL DMEM complete medium were plated in each well of a 48 well plate. After 24 h, Dox was added at concentrations of 0, 10, 30, 100, 300 ng/mL respectively. After 16 h, culture medium in supernatant was removed, and lysis was performed on ice for 10 min using 80 μL renilla luciferase lysate (purchased from Promega, E2820), lysate was mixed by pipetting, 50 μL cell lysate was transferred into a plate for luciferase detection (purchased from PE), 20 μL renilla luciferase substrate (purchased from Promega, E2820) was added into each well, and luciferase activity was detected by a microplate reader (purchased from Bio-Tek, SynergyH1). The remaining 30 μL lysate was used for immune blotting (Western Blotting), the primary antibody used was Anti-Gluc (purchased from NEB), the secondary antibody used was HRP-conjugated Donkey Anti-Rabbit (purchased from Jackson), and expression of PA/PB1 with Gluc fusion tag could be detected by a scanner (purchased from Bio-rad).

The results are shown in FIG. 1. When Dox was not added into the PA/PB1 HEK293T (Teton) cell line, luciferase activity of PA/PB1 interaction was the background. Expression of PA/PB1 with Gluc fusion tag increased with the increase in Dox concentration, meanwhile luciferase activity of PA/PB1 interaction increased gradually. When Dox was added at a concentration of 300 ng/mL, the difference between its signal value and the background signal value was up to 200 times. As the results show, PA/PB1 interaction can be detected by inducing the PA/PB1 HEK293T (Teton) cell line by Dox.

Detecting the Influence of Polypeptide on PA/PB1 Interaction by the PA/PB1 HEK293T (Teton) Cell Line A. Polypeptide fragments $PB1_{1-25}$, $PB1_{731-757}$ were cloned into a eukaryotic expression vector pFA-Flag-GFP. Specific primers were designed to amplify $PB1_{1-25}$, $PB1_{731-757}$ from a template pBD-PB1 (derived from highly pathogenic avian influenza A H5N1 virus gene isolated from geese in Guangdong Province in China in 1996, strain name: A/Goose/Guangdong/1/96(H5N1)). PCR primers were designed to synthesize PX gene, PCR products obtained by dual enzyme digestion using NdeI and BamHI (manufactured by NEB) was ligated to the vector pFA-Flag-GFP by T4 ligase enzyme, used for transformation of TOP10 competent cells, verified by sequencing and denoted as FA-PX-GFP, pFA-$PB1_{1-25}$-GFP, pFA-$PB1_{731-757}$-GFP herein; in other words, the Flag fragment in the pFA-Flag-GFP vector was replaced by PX, $PB1_{1-25}$, $PB1_{731-757}$ fragments.

B. Detecting the Influence of PX, $PB1_{1-25}$, $PB1_{731-757}$ on PA/PB1 Interaction in the PA/PB1 HEK293T (Teton) Cell Line PA/PB1 HEK293T (Teton) cells were plated in a 96 well plate. When the cells reached a density of 80%, 0.2 ug plasmids expressing PX, $PB1_{1-25}$ and $PB1_{731-757}$-GFP were transfected; after 12 h of transfection, 100 ng/ml Dox was added to induce the cells. After 12 h, the Gaussia Luciferase activity of the cells was measured. The value of samples containing PX was set to 100%, and other sample values were compared with PX. Results were shown in FIG. 2. When $PB1_{1-25}$-GFP was transfected, PA-PB1 interaction was significantly inhibited, and negative controls PX-GFP and $PB1_{731-757}$-GFP had little effect on the interaction. It is shown by our results that, the cell line can be used for detecting inhibitors against PA-PB1 interaction.

The present disclosure has a plurality of specific embodiments, and all technical solutions with equivalents and alternatives fall within the spirit and scope of the present disclosure.

What is claimed is:

1. A cell line for screening an influenza vims polymerase assembly inhibitor, wherein the cell line is a PA/PB1 HEK293T cell line with inducible PA/PB 1 expression, the PA/PB1 HEK293T cell line is formed by integrating a PA-GlucC fusion protein expression vector and a GlucN-PB1 fusion protein expression vector into a HEK293T cell, the HEK293T cell line is formed by ligating a synthesized Tetracycline-controlled Transcriptional Activation-3G gene fragment to a lentiviral vector FG and transferring into the HEK293T cell.

2. A construction method for a cell line to screen an influenza virus polymerase assembly inhibitor, wherein the construction method comprises the following steps, a. Amplify influenza vims PA, PB1 genes by specific primers, and amplification products are subjected to dual enzyme digestion, followed by ligation to a vector, and PA, PB1 full length plasmids are extracted;

b. Gaussia Luciferase is cloned into a lentiviral vector as a reporter gene;

c. By using the constructed PA, PB1 full length plasmids through clone techniques, PA, PB1 full length genes are integrated into the inducible lentiviral vector by homologous recombination to form pBiLC3-PA and pBiLC2-PB1;

d. An inducible gene fragment, which sequence is SEQ ID NO: 5, is ligated to the lentiviral vector FG, and denoted as FG-Teton-3G, and the HEK293T cell line is formed by stably expressing FG-Teton-3G in the ceil via a triple plasmid system of pMDLg/pRRE/, pRSV-Rev and pMD2.G;

e. PA/PB1 is stably integrated into the HEK293T cell by integrating the constructed pBiLC3-PA and pBiLC2-PBI into the HEK293T cell via the triple plasmid system, and finally, the PA/PB1 HEK293T cell line with inducible PA/PB1 expression is formed.

3. The construction method for the cell line to screen the influenza virus polymerase assembly inhibitor of claim 2, wherein sequences of the specific primers used for amplifying influenza virus polymerase are SEQ ID NO:1, SEQ ID NO:2, SEQ ID NO:3 and SEQ ID NO:4.

4. The construction method for the cell line to screen the influenza virus polymerase assembly inhibitor of claim 3, wherein the cell line is used for screening inhibitors against the interaction of polymerase subunits PA-PB1 of influenza virus.

* * * * *